(12) United States Patent
Sadana

(10) Patent No.: US 9,040,013 B2
(45) Date of Patent: May 26, 2015

(54) METHOD OF PREPARING FUNCTIONALIZED GRAPHENE

(75) Inventor: Anil K. Sadana, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 951 days.

(21) Appl. No.: 13/198,342

(22) Filed: Aug. 4, 2011

(65) Prior Publication Data

US 2013/0035500 A1 Feb. 7, 2013

(51) Int. Cl.
| | | |
|---|---|---|
| *C07C 68/00* | (2006.01) | |
| *C07C 67/30* | (2006.01) | |
| *C07C 45/00* | (2006.01) | |
| *C07C 17/32* | (2006.01) | |
| *C07C 231/12* | (2006.01) | |
| *B82Y 40/00* | (2011.01) | |
| *C07C 1/26* | (2006.01) | |
| *C01B 31/04* | (2006.01) | |

(52) U.S. Cl.
CPC . *B82Y 40/00* (2013.01); *C07C 1/26* (2013.01); *C01B 31/0484* (2013.01); *Y10S 977/896* (2013.01)

(58) Field of Classification Search
CPC C01B 31/04; C01B 31/0407; C01B 31/0415; C01B 2204/00; C01B 2204/02; C01B 2204/04; C01B 2204/06; C01B 2204/065; C01B 2204/20; C01B 2204/22; C01B 2204/24; C01B 2204/28
USPC ............... 423/448; 558/260; 570/190; 560/8; 564/123; 568/426; 977/896
See application file for complete search history.

(56) References Cited

U.S. PATENT DOCUMENTS

| | | | | |
|---|---|---|---|---|
| 3,404,061 | A * | 10/1968 | Bochman et al. ............. | 428/143 |
| 4,774,990 | A * | 10/1988 | Yamamoto et al. ............ | 164/14 |
| 5,279,873 | A | 1/1994 | Oike | |
| 6,882,094 | B2 | 4/2005 | Dimitrijevic et al. | |
| 7,048,048 | B2 | 5/2006 | Nguyen et al. | |
| 7,112,361 | B2 | 9/2006 | Lynn et al. | |
| 7,745,528 | B2 | 6/2010 | Prud'Homme et al. | |
| 7,758,841 | B2 | 7/2010 | Billups et al. | |
| 2004/0013597 | A1 | 1/2004 | Mao et al. | |
| 2004/0018364 | A1 | 1/2004 | Ota et al. | |
| 2004/0053037 | A1 | 3/2004 | Koch et al. | |
| 2004/0229983 | A1 | 11/2004 | Winowiecki | |
| 2005/0001317 | A1 | 1/2005 | Ganapathiraman et al. | |
| 2005/0070655 | A1 | 3/2005 | Van Den Bergen et al. | |
| 2005/0161212 | A1 | 7/2005 | Leismer et al. | |
| 2006/0199770 | A1 | 9/2006 | Bianco et al. | |
| 2007/0003471 | A1 | 1/2007 | Kawabata | |
| 2007/0107908 | A1 | 5/2007 | Vaidya et al. | |
| 2007/0142547 | A1 | 6/2007 | Vaidya et al. | |
| 2007/0237546 | A1 | 10/2007 | Zona et al. | |
| 2008/0087431 | A1 | 4/2008 | Willauer et al. | |
| 2008/0127475 | A1 | 6/2008 | Griffo | |
| 2008/0149363 | A1 | 6/2008 | Han et al. | |
| 2008/0220282 | A1 | 9/2008 | Jang et al. | |
| 2008/0306225 | A1 | 12/2008 | Prud'homme et al. | |
| 2009/0036605 | A1 | 2/2009 | Ver Meer | |
| 2009/0155578 | A1 | 6/2009 | Zhamu et al. | |
| 2009/0198009 | A1 | 8/2009 | Matsuki et al. | |
| 2009/0308520 | A1 | 12/2009 | Shin et al. | |
| 2010/0021708 | A1 | 1/2010 | Kong et al. | |
| 2010/0047154 | A1 * | 2/2010 | Lee et al. ....................... | 423/460 |
| 2010/0059726 | A1 | 3/2010 | Jung et al. | |
| 2010/0096595 | A1 | 4/2010 | Prud'Homme et al. | |
| 2010/0130701 | A1 | 5/2010 | Lahdensuo | |
| 2010/0159366 | A1 | 6/2010 | Shao-Horn et al. | |
| 2010/0163844 | A1 | 7/2010 | Ermolov | |
| 2010/0178464 | A1 | 7/2010 | Choi et al. | |
| 2010/0179645 | A1 | 7/2010 | Chen et al. | |
| 2010/0314118 | A1 | 12/2010 | Quintero et al. | |
| 2011/0067872 | A1 | 3/2011 | Agrawal | |
| 2011/0200674 | A1 | 8/2011 | MacKay | |
| 2011/0232901 | A1 | 9/2011 | Carrejo et al. | |

FOREIGN PATENT DOCUMENTS

| | | | |
|---|---|---|---|
| KR | 10-2004-0095581 | A | 11/2004 |
| KR | 10-0620615 | B1 | 9/2006 |
| KR | 10-2007-0053164 | A | 5/2007 |
| KR | 10-2009-0014186 | A | 2/2009 |
| KR | 10-2009-0086536 | A | 8/2009 |
| WO | 03/103854 | A1 | 12/2003 |
| WO | 2008/048705 | A2 | 4/2008 |
| WO | 2008045778 | A1 | 4/2008 |
| WO | 2008130431 | A2 | 10/2008 |
| WO | 2010002770 | A1 | 1/2010 |

OTHER PUBLICATIONS

Scientific Background on the Nobel Prize in Physics 2010—Graphene—compiled by the Class for Physics of the Royal Swedish Academy of Sciences, The Royal Swedish Academy of Sciences, pp. 1-10 (Oct. 5, 2010).*
Singh, et al., Organic functionalization and characterization of single-walled carbon nanotubes, Chemical Society Reviews 2009; 38: 2214-2230.*
Pekker, et al., Hydrogenation of Carbon Nanotubes and Graphite in Liquid Ammonia, J. Phys. Chem. B. 2001; 105: 7938-7943.*
Borondics, et al., Fucntionalization of Carbon Nanotubes via Dissolving Metal Reductions, J. Nanoscience and Nanotechnology 2007; 7: 1551-1559.*
Thierry Cassagneau et al., "Preparation and Characterization of Ultrathin Films Layer-by-Layer Self-Assembled from Graphite Oxide Nanoplatelets and Polymers"; Langmuir 2000 16 (18), 7318-7324.
Aravind Dasari et al., "Fundamental aspects and recent progress on wear/scratch damage in polymer nanocomposites," Materials Science and Engineering R 63 (2009) 31-80.
Christopher A. Dyke et al., "Covalent Functionalization of Single-Walled Carbon Nanotubes for Materials Applications," The Journal of Physical Chemistry; vol. 108, No. 51, Dec. 23, 2004, pp. 11151-11159.
Jinni Deng et al., "Mechanical and Surface Properties of Polyurethane/Fluorinated Multi-Walled Carbon Nanotubes Composites," Journal of Applied Polymer Science DOI 10.1002/app. 27625, Published online Feb. 4, 2008 in Wiley InterScience (www.interscience.wiley.com), pp. 2023-2028.

(Continued)

*Primary Examiner* — Daniel C McCracken
(74) *Attorney, Agent, or Firm* — Cantor Colburn LLP

(57) ABSTRACT

A method of preparing functionalized graphene, comprises treating graphene with an alkali metal in the presence of an electron transfer agent and coordinating solvent, and adding a functionalizing compound. The method further includes quenching unreacted alkali metal by addition of a protic medium, and isolating the functionalized graphene.

24 Claims, No Drawings

(56) References Cited

OTHER PUBLICATIONS

International Search Report and Written Opinion for International Application No. PCT/US2011/043033; Mailed Mar. 22, 2012; 11 pages.

International Search Report and Written Opinion for International Application No. PCT/US2011/050956; Mailed Apr. 30, 2012; 10 pages.

Borondics, et al.; "Functionalization of Carbon Nanotubes Via Dissolving Metal Reductdions"; Journal of Nanoscience and Nanotechnology; 7; pp. 1551-1559; (2007).

Busick, et al., "Effects of graphite content on the morphology and barrier properties of poly(vinylidene fluoride) composites," Polymer 40: 6023-6029 (1999).

Chakraborty, et al.; "Reductive Alkylation of Fluorinated Graphite"; Chem. Mater.; 20; pp. 3134-3136; (2008).

Chattopadhyay, et al.; "Carbon Nanotube Salts. Arylation of Single-Wall Carbon Nanotubes"; Organic Letters; 7 (19); pp. 4067-4069; (2005).

William S. Hummers Jr., et. al.; Preparation of Graphitic Oxide; J. Am. Chem. Soc.; 1957; p. 1339.

Hannes C. Schniepp, et. al.; Functionalized Single Graphene Sheets Derived from Splitting Graphite Oxide; The Journal of Physical Chemistry Letters, vol. 110; 2006; pp. 8535-8539.

Lee et al.; "Layer-by-Layer Assembly of All Carbon Nanotube Ultrathin Films for Electrochemical Applications"; J. Am. Chem. Soc., 131 (2); pp. 671-679; (2009).

Liang, et al.; "A Convenient Route to Functionalized Carbon Nanotubes"; Nano Letters; 4(7); pp. 1257-1260; (2004).

Nina I. Kovtyukhova, et. al.; Layer-by-Layer Assembly of Ultrathin Composite Films from Micron-Sized Graphite Oxide Sheets and Polycations; Chem. Mater, vol. 11, No. 3; 1999; pp. 771-778.

Sasha Stankovich, et. al. Graphene-based composite materials; Nature 04969, vol. 442; 2006; pp. 282-286.

Shen, et al.; "Layer-by-Layer Self-Assembly of Graphene Nanoplatelets"; Langmuir; 25(11), pp. 61-22-6128; (2009).

Woo-Sik Jang, et. al.; Layer-by-layer assembly of thin film oxygen barrier; Thin Solid Films, vol. 516; 2008; pp. 4819-4825.

Stephenson, et al.; "Highly Functionalized and Soluble Multiwalled Carbon Nanotubes by Reductive Alkylation and Arylation: The Billups Reaction"; Chem. Mater.; 18; pp. 4658-4661; (2006).

Mitchell et al. "Dispersion of Functionalized Carbon Nanotubes in Polystyrene", Macromolecules 2002, 35, 8825-8830.

Extended European Search Report for related EP Application No. 11745232.6-1303 / 2536561, dated Feb. 6, 2014, pp. 1-8.

International Search Report and Written Opinion; International Application No. PCT/US2012/069098; International Filing Date: Dec. 12, 2012; Date of Mailing: Mar. 15, 2013; 12 pages.

N.V. Sirotinkin et al., "Model of Formation of Three-Dimensional Polyurethane Films Modified by Detonation Nanodiamonds," Physics of the Solid State, vol. 46, 2004, pp. 746-747. Translated from Fizika Tverdogo Tela, vol. 46, 2004, pp. 725-726.

International Search Report and Written Opinion; International Application No. PCT/US2012/0024094; International Filing Date: Feb. 7, 2012; Date of Mailing: Sep. 3, 2012; 7 pages.

Office Action for related Gulf Co-Operation Application No. GC 2011-17807, dated Sep. 21, 2014, pp. 1-18.

* cited by examiner

METHOD OF PREPARING FUNCTIONALIZED GRAPHENE

BACKGROUND

Nanoparticles generally have increasingly found use in a variety of new applications, from composite materials with different physical properties, to improved electronic devices. With the increase in availability and decreasing cost of nanoparticles, which are becoming available in relative quantity compared to several years ago, there is greater interest in tailoring the properties of nanoparticles to further suit the needs of more advanced applications.

Derivatization of nanoparticles to alter their properties and adjust their environmental interactions has been examined for reactivity and suitable conditions, including those of carbonaceous nanoparticles such as nanotubes, nanographite, carbon black, etc. For example, U.S. Patent Application Publication No. 2010/0592463 discloses the derivatization of carbon particles including nanotubes under conditions of reductive alkylation (sometimes referred to in the art as reductive amination). However, such reactions, which use standard dissolving metal techniques in liquid ammonia, require low temperatures and are not generally readily scaled. Furthermore, liquid ammonia can react with certain functional groups such as esters, anhydrides, and acid chlorides, and hence is not compatible with such functional groups.

SUMMARY

The above and other deficiencies in the prior art can be overcome by, in an embodiment, a method of preparing functionalized graphene, including treating graphene with an alkali metal in the presence of a coordinating solvent, and adding a functionalizing compound.

In another embodiment, a method of preparing functionalized graphene includes dissolving an alkali metal, in a coordinating solvent, adding graphene, and adding a functionalizing compound.

In another embodiment, a method of preparing functionalized graphene, includes combining tetrahydrofuran with naphthalene, dissolving an alkali metal, in the combination of tetrahydrofuran and naphthalene, adding graphene, and adding a functionalizing compound.

DETAILED DESCRIPTION OF THE INVENTION

Disclosed herein is a novel method for functionalizing graphene. In the method, graphene, which has an extended pi-electron system similar to that of nanotubes, but without interspersed five membered rings in the extended system, has been found to be derivatizable using dissolving metal techniques but without need for the use of liquid ammonia to dissolve the metal (i.e., an alkali metal). Instead, a coordinating solvent, e.g., an ether such as tetrahydrofuran, is used to assist in solvation, and to stabilize the metallated graphene intermediate. In addition, an aromatic such as naphthalene is included as an electron transfer agent to transfer electrons from the alkali metal (e.g., sodium) to the graphene, and the resulting anion treated with an anion-reactive compound to effect the modification. In this way, graphene is functionalized by modified Birch reduction without the use of ammonia or other amine solvents, particularly primary or secondary amines. The resulting method is a versatile, safer and more scalable method for functionalization of graphene.

The method of preparing functionalized graphene thus includes treating graphene with an alkali metal in the presence of a coordinating solvent, and adding a functionalizing compound.

Graphene, including nanographene and graphene fibers, are derivatized according to the method disclosed herein. Graphene and nanographene are effectively two-dimensional particles of nominal thickness, having of one or more layers of fused hexagonal rings of carbon atoms with an extended delocalized π-electron system, layered and weakly bonded to one another through π-π stacking interaction. Graphene in general, and including nanographene, can in one embodiment be a single sheet, or in another embodiment be a stack of several sheets of such extended carbon rings. The sheets have, in some embodiments, micro-scale dimensions (i.e., an average particle size of less than about 1 µm); nano-scale, (i.e., an average particle size of greater than or equal to about 1 µm); or both micro- and nano-scale dimensions. As used herein, "average particle size" refers to the number average particle size based on the largest linear dimension of the particle (sometimes referred to as "diameter"). Particle size, including average, maximum, and minimum particle sizes, may be determined by an appropriate method of sizing particles such as, for example, static or dynamic light scattering (SLS or DLS) using a laser light source.

For example, in some embodiments, graphene has an average particle size of about 1 to about 20 µm, specifically about 1 to about 15 µm, and an average thickness (smallest) dimension in nano-scale dimensions of less than or equal to about 50 nm, specifically less than or equal to about 25 nm, and more specifically less than or equal to about 10 nm. An exemplary nanographene has an average particle size of about 1 to 10 µm, and specifically 2 to 8 µm.

Graphenes of different average particle size are useful, and in this way, the particle size distribution of the graphene is unimodal (exhibiting a single distribution), bimodal exhibiting two distributions, or multi-modal, exhibiting more than one particle size distribution. For example, smaller nanographenes (of less than about 250 nm) and including sub-micron sized graphene (about 250 nm to less than about 1 µm) can be combined with graphene having an average particle size of greater than or equal to 1 µm. Graphene fibers (i.e., graphene particles having an average largest dimension of greater than 1 mm and an aspect ratio of greater than 10, where the graphene particles form an interbonded chain), are also functionalized using the method disclosed herein.

Graphene can be of various dimensions, predominantly having a two-dimensional aspect ratio (i.e., ratios of length to width, at an assumed thickness; diameter to thickness; or surface area to cross-sectional area, for plate-like graphene, of greater than or equal to 10, specifically greater than or equal to 100, more specifically greater than or equal to 200, and still more specifically greater than or equal to 500. Similarly, the two-dimensional aspect ratio is less than or equal to 10,000, specifically less than or equal to 5,000, and still more specifically less than or equal to 1,000.

The nanographene is formed by exfoliation from a graphite source. In an embodiment, graphene is formed by exfoliation of graphite, intercalated graphite, and nanographite. Exemplary exfoliation methods include, but are not limited to, those practiced in the art such as fluorination, acid intercalation, acid intercalation followed by thermal shock treatment, and the like. It will be appreciated that exfoliation of graphite can provide graphene as a single sheet only one molecule thick, or as a layered stack of relatively few sheets. In an embodiment, exfoliated graphene has fewer than 50 single sheet layers, specifically fewer than 20 single sheet layers, specifically fewer than 10 single sheet layers, and more specifically fewer than 5 single sheet layers.

Graphene, including nanographene, can be prepared by exfoliation of nanographite or by a synthetic procedure by "unzipping" a nanotube to form a nanographene ribbon, followed by functionalization of the graphene.

Exfoliation to form graphene or nanographene is carried out by exfoliation of a graphite source such as graphite, intercalated graphite, and nanographite. Exemplary exfoliation methods include, but are not limited to, those practiced in the art such as fluorination, acid intercalation, acid intercalation followed by thermal shock treatment, and the like, or a combination comprising at least one of the foregoing. Exfoliation of the nanographite provides a nanographene having fewer layers than non-exfoliated nanographite. It will be appreciated that exfoliation of nanographite provides the nanographene as a single sheet only one molecule thick, or as a layered stack of relatively few sheets. In an embodiment, exfoliated nanographene has fewer than 50 single sheet layers, specifically fewer than 20 single sheet layers, specifically fewer than 10 single sheet layers, and more specifically fewer than 5 single sheet layers.

The minimum particle size for the smallest 5 percent of graphene is less than 0.05 nm, specifically less than or equal to 0.02 nm, and more specifically less than or equal to 0.01 nm. Similarly, the maximum particle size for 95% of the graphene is greater than or equal to 900 nm, specifically greater than or equal to 750 nm, and more specifically greater than or equal to 500 nm. The graphene particles have a high surface area of greater than 300 $m^2/g$, specifically 300 $m^2/g$ to 1800 $m^2/g$, and more specifically 500 $m^2/g$ to 1500 $m^2/g$.

The graphene is treated with an alkali metal and a coordinating solvent. "Treating", as used herein, generally includes contacting the graphene to a solution of alkali metal dissolved in the coordinating solvent. In doing so, a free, "solvated" electron is transferred from the solution directly or indirectly (as through an electron transfer compound, described further hereinbelow) to the graphene, which then forms a pi-stabilized anion radical. The alkali metal is, in an embodiment, lithium, sodium, potassium, an alloy thereof, or a combination comprising at least one of the foregoing. In an exemplary embodiment, the alkali metal is sodium. It will be understood by the skilled artisan that the stoichiometry of the alkali metal to the graphene is not particularly limited as the graphene can be substituted with one or more substituents, and hence the molar amount of alkali metal used depends on the degree of substitution of the graphene desired.

The alkali metal is dissolved in a coordinating solvent. The coordinating solvent comprises an ether, an amine, or a combination comprising at least one of the foregoing. In a specific embodiment, the coordinating solvent is an ether and/or tertiary amine. In a specific embodiment, the coordinating solvent is not ammonia. The coordinating solvent is aprotic, and is substantially free of protic contaminants such as moisture, alcohols, protic amines (primary and secondary), hydroperoxides, or other reactive species including carbonyl compounds such as acids, ketones, aldehydes, esters, and the like.

Where the coordinating solvent is an ether, any ether can be used so long as it does not react with the alkali metal. Useful ethers include alkyl or cycloalkyl ethers. Exemplary ethers include tetrahydrofuran, dioxane, diethyl ether, diisopropyl ether, di-n-butyl ether, di-sec-butyl ether, methyl-t-butyl ether, 1,2-dimethoxyethane, 1,2-dimethoxypropane, 1,3-dimethoxypropane, 1,2-diethoxyethane, 1,2-diethoxypropane, 1,3-diethoxypropane, or a combination comprising at least one of the foregoing.

Amines useful as coordinating solvents include tertiary amines. Useful amines are tertiary alkyl or cycloalkyl amines. Exemplary such amines include tertiary amine including n-methyl piperidine, n-methyl morpholine, N,N,N',N'-tetramethyl-1,2-diaminoethane, or a combination comprising at least one of the foregoing.

A non-coordinating solvent can further be included in addition to the coordinating solvent during treating. The non-coordinating solvent is, in an embodiment, a non-reactive, aprotic hydrocarbon solvent. Exemplary such solvents include hexanes, heptanes, octanes including n-octane and 2,2,4-trimethyl pentane, cyclopentane, methylcyclopentane, ethylcyclopentane, cyclohexane, methylcyclohexane, petroleum ether including naphtha and ligroin, and the like, or a combination of these.

The anion-reactive compound is an alkyl halide, aralkyl halide, ester, amide, carbonate, aldehyde, unsaturated ester, or a combination comprising at least one of the foregoing. Exemplary anion-reactive compounds include $C_{1-30}$ alkyl halides, $C_{1-30}$ carbonyl compounds including acids, esters, amides, anhydrides, ketones, carbonates, aldehydes, and the like; $C_{1-30}$ cyclocarbonyl compounds including lactones, carbonates, cyclic ketones, and the like, or a combination comprising at least one of the foregoing. Exemplary such anion-reactive compounds include haloalkanes such as chloro-, bromo-, and iodo-ethane, propane, butane, pentane, hexane, octane, nonane, decane, dodecane, and the like. Other anion-reactive compounds useful herein include carbon dioxide, peroxides, epoxides, and the like. The anion-reactive compound can, in an embodiment, be bifunctional, including for example both halogen functionality and carbonyl functionality. For example, useful anion-reactive compound that are bifunctional include omega haloacids such as bromoacetic acid, omega haloaliphatic acids such as 10-bromodecanoic acid, 12-bromododecanoic acid, and the like, but are not limited to these. It will be appreciated that the functionalized graphene can be further derivatized to change the functional group to a different functional group, without limitation.

The graphene, so functionalized, includes functional groups such as carboxy, epoxy, ether, ketone, amine, hydroxy, alkoxy, alkyl, lactone, aryl, functionalized polymeric or oligomeric groups, or a combination comprising at least one of the forgoing functional groups, depending on the anion radical reactive compound used. In an exemplary embodiment, graphene is functionalized with alkyl groups, carboxylic acid groups, polymeric groups, or the like. Also in an embodiment, the graphene after functionalization comprises about 0.1 to about 75 wt%, more specifically about 1 to about 50 wt%, more specifically about 2 to about 25 wt%, and still more specifically about 5 to about 20 wt% of functional group, based on the total weight of the functionalized graphene.

The alkali metal and the functionalizing compound are present in stoichiometric amounts. In an embodiment, the alkali metal and the functionalizing compound are present in a molar ratio of about 1.2:1 to 1:1.2, specifically, in a molar ratio of about 1.1:1 to 1:1.1, and still more specifically, in a molar ratio of about 1.05:1 to 1:1.05 respectively. Treating is carried out for any amount of time necessary to effectively ensure quantitative electron transfer from the reaction medium to the graphene. In an embodiment, treating is carried out for less than or equal to about 1 hour, specifically less than or equal to about where it will be appreciated that this time period commences from the time of adding the graphene to the reaction mixture. In a further embodiment, where an electron transfer agent is used, the alkali metal and the electron transfer agent are present in a molar ratio of about 1.2:1 to 1:1.2, specifically, in a molar ratio of about 1.1:1 to 1:1.1, and still more specifically, in a molar ratio of about 1.05:1 to 1:1.05 respectively.

In an embodiment, treating further and more specifically comprises dissolving the alkali metal in the coordinating solvent, followed by adding the graphene. In a further embodiment, an electron transfer agent is included with the solvent. In an embodiment, treating thus further comprises adding an electron transfer agent to the coordinating solvent prior to dissolving the alkali metal. A useful electron transfer agent includes, for example, naphthalene, anthracene, phenanthrene, and the like. In an exemplary embodiment, the electron transfer agent is naphthalene.

The reaction is run in the absence of oxygen. In an embodiment, the reaction is run under inert atmosphere including nitrogen, argon, or the like, or a combination comprising at least one of the foregoing. In an embodiment, oxygen is present in an amount less than 100 ppm, specifically less than 10 ppm, and more specifically less than 1 ppm, based on volume. It is noted that where lithium is the alkali metal, it is not desirable to run the reaction under nitrogen, which reacts with the lithium to produce lithium nitride.

In an embodiment, the method further includes quenching unreacted alkali metal by addition of a protic medium, and isolating the functionalized graphene. The protic medium can be, for example, an alcohol, water, or a combination of these. For example, where a combination is used, the quench can be carried out by initially adding an alcohol, which has a lower reactivity toward any unreacted dissolved alkali metal, followed by water, and/or by an acid. In an exemplary procedure, a quench is carried out by adding an alcohol such as methanol or ethanol, followed by water or dilute hydrochloric acid. It will be appreciated that the method of quench is only illustrated by these, and is not limited thereto.

In another embodiment, the method of preparing functionalized graphene, comprises dissolving an alkali metal, in a coordinating solvent, adding graphene, and adding a functionalizing compound. In another embodiment, the method includes combining tetrahydrofuran, with naphthalene, dissolving an alkali metal in the combination of tetrahydrofuran and naphthalene, adding graphene, and adding a functionalizing compound.

It will be further appreciated that treating and functionalizing (by addition of the functionalizing compound)

The above and other embodiments are further illustrated in the following examples, which are illustrative but are not to be considered as limited thereto.

Preparation of dodecyl-functionalized graphene. Graphene (nXGP, 5 μm average particle size, available from XG Sciences) was functionalized by a modified Birch reduction using tetrahydrofuran (THF) and sodium metal as follows. A flame dried 250 ml three neck flask equipped with a stir bar and stoppers was charged with 200 ml of anhydrous, distilled THF (distilled from sodium benzophenone ketyl) by cannula under an argon atmosphere. To the THF was added 4.26 g (33.33 mmol) of naphthalene as an electron transfer agent with stirring for 15 minutes until the naphthalene dissolved. Freshly cut Na pieces (0.76 g, 33.33 mmol) were then added, and the mixture was stirred for 30 minutes, during which time the solution became green color due to solvation of the electrons. Graphene (200 mg; previously dried in vacuo) was added to the reaction flask, and was stirred for 30 minutes. Dodecyl iodide (9.86 g, 33.33 mmol) was then added by syringe through a septum. The reaction was then stirred at room temperature for 48 hours, at which time ethanol was added to quench any remaining unreacted sodium in the reaction vessel, after which the reaction mixture was quenched with 10 ml dilute (0.1 M aq.) HCl, and stirred for an additional 30 minutes and then transferred to reparatory funnel. Hexanes (50 ml) were added to separate the functionalized graphene from the aqueous layer (where the functionalized graphene was suspended at the interface of the aqueous and organic phases). The aqueous layer was removed, and the organic (hexane-containing) layer containing the functionalized graphene-containing interlayer was washed (3×100 ml) with water until colorless. The precipitated dodecyl functionalized graphene was collected by filtration of the organic layer/suspension layer on a 0.45 μm polytetrafluoroethane (PTFE) filter and repeatedly washed with a 70:30 (v/v) mixture of ethanol and hexanes.

Thermogravimetric analysis (TGA) was performed on TA Instruments Q 500 Thermogravimetric Analyzer. The sample was heated at 110° C. for 30 minutes, then heated to 850° C. at a ramp rate of 10° C./min. The sample showed weight loss of 16 wt % corresponding to loss of the functionality.

Thermal Conductivity. The dodecyl-functionalized graphene obtained by the method developed above was dispersed in electrical submersible pump (ESP) motor oil (CL-7, obtained from Centerlift, Inc.) and evaluated for thermal conductivity and stability. A dispersion of dodecyl-functionalized graphene (0.8 wt%) was prepared. There was on visible separation of the dodecyl-functionalized graphene upon standing. The thermal conductivity of the sample was carried out using a Hot Disk® TSP 500Thermal Constants Analyzer by ThermTest Inc., and was found to be is 19× higher when tested at both 100° C. and 150° C. than the control CL-7 ESP motor oil, which remain unchanged at these temperatures.

While one or more embodiments have been shown and described, modifications and substitutions may be made thereto without departing from the spirit and scope of the invention. Accordingly, it is to be understood that the present invention has been described by way of illustrations and not limitation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All ranges disclosed herein are inclusive of the endpoints, and the endpoints are independently combinable with each other. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like. All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The invention claimed is:

1. A method of preparing functionalized graphene, comprising:
   treating
      graphene, with
      an alkali metal,
   in the presence of a coordinating solvent, and
   adding a functionalizing compound,
      wherein that the coordinating solvent comprises at least one of an ether or a tertiary amine; and
      wherein the coordinating solvent is free of ammonia.

2. The method of claim 1, wherein the graphene has an average particle size of less than about 1 micrometer.

3. The method of claim 1, wherein the graphene has an average particle size of greater than or equal to about 1 micrometer.

4. The method of claim 3, wherein the graphene has an average particle size of about 1 to about 10 micrometers.

5. The method of claim 1, wherein the graphene has a two-dimensional aspect ratio of greater than about 10.

6. The method of claim 1, wherein the graphene is exfoliated by fluorination, acid intercalation, acid intercalation followed by thermal shock treatment, or a combination comprising at least one of the foregoing.

7. The method of claim 1, wherein the alkali metal is lithium, sodium, or potassium.

8. The method of claim 1, wherein the ether is tetrahydrofuran, dioxane, diethyl ether, diisopropyl ether, di-n-butyl ether, di-sec-butyl ether, methyl-t-butyl ether, 1,2-dimethoxyethane, 1,2-dimethoxypropane, 1,3-dimethoxypropane, 1,2-diethoxyethane, 1,2-diethoxypropane, 1,3-diethoxypropane, or a combination comprising at least one of the foregoing.

9. A method of preparing functionalized graphene, comprising:
   treating
      graphene, with
      an alkali metal,
   in the presence of a coordinating solvent, and
   adding a functionalizing compound, wherein the coordinating solvent comprises at least one of an ether; or an amine; and wherein the amine comprises a tertiary amine.

10. The method of claim 9, wherein the tertiary amine is n-methyl piperidine, n-methyl morpholine, N,N,N',N'-tetramethyl-1,2-diaminoethane, or a combination comprising at least one of the foregoing.

11. The method of claim 1, further comprising a non-coordinating solvent.

12. The method of claim 11, wherein the non-coordinating solvent is a hydrocarbon solvent.

13. The method of claim 1, wherein treating is carried out at less than or equal to ambient temperature.

14. The method of claim 1, wherein the functionalizing compound comprises an alkyl halide, aralkyl halide, ester, amide, carbonate, aldehyde, unsaturated ester, or a combination comprising at least one of the foregoing.

15. The method of claim 1, wherein treating comprises dissolving the alkali metal in the coordinating solvent, followed by adding the graphene.

16. The method of claim 15, wherein treating further comprises adding an electron transfer agent to the coordinating solvent prior to dissolving the alkali metal.

17. The method of claim 1, wherein the alkali metal and the functionalizing compound are present in a molar ratio of about 1.2:1 to 1:1.2, respectively.

18. The method of claim 1, wherein treating is carried out for less than or equal to 1 hour.

19. The method of claim 1, further comprising:
   quenching unreacted alkali metal by addition of a protic medium, and
   isolating the functionalized graphene.

20. The method of claim 1, wherein the functionalized graphene has functional groups including carboxy, epoxy, ether, ketone, amine, hydroxy, alkoxy, alkyl, lactone, aryl, functionalized polymeric or oligomeric groups, or a combination comprising at least one of the forgoing functional groups.

21. A method of preparing functionalized graphene, comprising:
   dissolving
      an alkali metal, in
      a coordinating solvent,
   adding graphene, and
   adding a functionalizing compound,
      wherein that the coordinating solvent comprises an ether, a tertiary amine, or a combination comprising at least one of the foregoing; and
      wherein the coordinating solvent is free of ammonia.

22. A method of preparing functionalized graphene, comprising:
   combining
      tetrahydrofuran, with
      naphthalene,
   dissolving
      an alkali metal, in the combination of tetrahydrofuran and naphthalene,
   adding graphene, and
   adding a functionalizing compound.

23. The method of claim 22, wherein the alkali metal comprises sodium.

24. The method of claim 1, wherein the ether is dioxane, diethyl ether, diisopropyl ether, di-n-butyl ether, di-sec-butyl ether, methyl-t-butyl ether, 1,2-dimethoxyethane, 1,2-dimethoxypropane, 1,3-dimethoxypropane, 1,2-diethoxyethane, 1,2-diethoxypropane, 1,3-diethoxypropane, or a combination comprising at least one of the foregoing.

* * * * *